US008581028B2

(12) United States Patent
Langham

(10) Patent No.: US 8,581,028 B2
(45) Date of Patent: Nov. 12, 2013

(54) METHOD FOR BREEDING IMPROVED NON-DEHISCENT SESAME

(75) Inventor: Derald Ray Langham, San Antonio, TX (US)

(73) Assignee: Sesaco Corporation, Austin, TX (US)

( * ) Notice: Subject to any disclaimer, the term of this patent is extended or adjusted under 35 U.S.C. 154(b) by 316 days.

(21) Appl. No.: 12/946,714

(22) Filed: Nov. 15, 2010

(65) Prior Publication Data

US 2011/0067135 A1     Mar. 17, 2011

Related U.S. Application Data

(62) Division of application No. 12/041,257, filed on Mar. 3, 2008, now Pat. No. 8,080,707.

(51) Int. Cl.
*A01H 1/04*     (2006.01)
*A01H 1/00*     (2006.01)

(52) U.S. Cl.
USPC ............................ 800/266; 800/265; 800/260

(58) Field of Classification Search
None
See application file for complete search history.

(56) References Cited

U.S. PATENT DOCUMENTS

| 6,100,452 | A * | 8/2000 | Langham | ...................... 800/298 |
| 6,781,031 | B2 | 8/2004 | Langham | |
| 6,815,576 | B2 | 11/2004 | Langham | |
| 7,148,403 | B2 | 12/2006 | Langham | |
| 7,332,652 | B2 | 2/2008 | Langham | |

FOREIGN PATENT DOCUMENTS

| WO | WO9915681 | 4/1999 |
| WO | WO0013488 | 3/2000 |

OTHER PUBLICATIONS

Ashri, A. 1998. "Sesame Breeding," Plant Breeding Rev. 16:179-228.
Ashri, A. 1980. "Sesame," Oil Crops of the World, Chap. 18, pp. 375-387; McGraw-Hill Publishing, Co., New York.
Bakheit, et al. 1996. "Inheritance of Some Qualitative and Quantitative Characters in *Sesamum idicum* L.," Assuit Journal of the Agricultural Sciences 27:27-41.
Day, Jamie. 1998 "The mechanism of indehiscence in Sesame. Features that might be useful in a breeding programme," Third FAO/IAEA Research Coordination meeting on Induced Mutations for Sesame Improvements, Bangkok, Thailand; Apr. 6-19, 1998; 11pp.
Delgado, et al. 1992. "Analisis Del Cruzamiento Dialelico De Seis Variedades Indehiscentes Y Dos Dehiscentes de Ajonjoli *Sesamum indicum* L." Agronomia Tropical 42:191-210.
Hutson, B.D. 1983. "Standards for the inspection and grading of sesame seed," Hutson Laboratories, Yuma, Arizona, pp. 1-5.
IBPGR Secretariat. 1981. "Descriptor for Sesame," International Board for Plant Genetic Resources, Rome, pp. 1-19.
Kalton, R.R. 1949. "A promising new oilseed crop for Texas," Proc First International Sesame Conference, Clemson Agricultural College, Clemson, South Carolina, pp. 62-66.
Langham, D.R. 2007. "Phenology of Sesame," Issues in New Crops and New Uses, Janick & Whipkey, eds., ASHS Press, Alexandria, VA, pp. 144-182.
Langham, D.G. 1944. "Natural and controlled pollination in sesame," Journal of Heredity 8:254-256.
Langham, D.G. and Rodriguez, J. 1949. "Improvements in Sesame in Venezuela," Proc. First Intern'l Sesame Conf., Clemson Agri. College, Clemson, South Carolina, pp. 74-79.
Langham, et al. 1956. "Dehiscencia Y otras caracteristicas del ajonjoli, *Sesamum indicum* L., en relacion con el problema de la cosecha," Gensa, Maracay, Venezuela; pp. 3-16.
Langham, D.R. 1998. "Shatter resistance in Sesame," Third FAO/IAEA Res. Co-ord. Mtng on Induced Mutations for Sesame Improvements, Bangkok, Thailand, Apr. 6-10, 1998; 14 pages.
Langham, D.R. 2001. "Shatter resistance in sesame," In: L. Van Zanten (ed.), Sesame improvements by induced mutations, Proc. Final FAO/IAEA Coordination Research Meeting, IAEA, Vienna TECDOC 1195, pp. 51-61.
Langham, D.R. & Wimers, T. 2002. "Progress in mechanizing sesame in the U.S. through breeding," Trends in Crops and New Uses, J. Janick & A. Whipkey (eds.), ASHA Press Alexandria, VA; pp. 157-173.
Namiki, Mitsuo. 1995. "The Chemistry and Physiological Functions of Sesame," Food Reviews International, 11:281-329.
Osman, H.E. 1985. "Studies in sesame: hybridization and related techiniques," FAO Plant Production and Protection Paper No. 66, pp. 145-156.
"Recommendations for the Discussion Groups," 1995. Proceedings of Sesame Workshop, Darwin and Katherine, Northern Territory, Australia, Mar. 12-23, 1995, pp. 252-257.
Shigeo, et al. 1994. "Breeding of good quality sesame with dehiscence resistance and strong antioxidative property," Baiorunessansu Keikaku (abstract only).
Wongyai, W. & Juttpornpong, S. 1992 Indirect selection for seed weight in sesame using capsule size as a criteria, Sesame and Safflower Newsletter, No. 7, pp. 4-7.

(Continued)

*Primary Examiner* — Cathy Kingdon Worley
(74) *Attorney, Agent, or Firm* — Hemingway & Hansen LLP; D. Scott Hemingway

(57) ABSTRACT

Methods for improving the agriculture of sesame, an Improved Non-Dehiscent (IND) sesame class and methods for breeding IND are disclosed. The IND sesame holds its seed in capsules for four or more weeks after ideal harvesting time, during extended adverse weather conditions, thus offering the grower flexibility as to when to harvest. The methods also improve current agricultural methods for growing sesame by allowing growers to leave the crop in the field for a longer period of time without the loss of seeds and concomitant reduced yield. The grower is able to reduce the ratio of combine harvesters required for mechanical harvest of sesame crops. Further, a method of growing crops in geographical areas previously unsuitable for sesame agriculture is disclosed. IND allows ready release of seed from the capsule during mechanized harvesting with minimal broken seed.

4 Claims, 6 Drawing Sheets

(56) References Cited

OTHER PUBLICATIONS

Weiss, E.A. 1971. "History," Castor, Sesame and Safflower, Leonard-Hill Books, London; pp. 311-525.

Weiss, E.A. 1983. "Sesame," Oilseed Crops, Longman Inc., New York, pp. 282-340.

Weiss. 2000. "Sesame," Oilseed Crops, Longman Inc., New York, pp. 131-164.

Yermanos, D.M. 1980. "Sesame," Hybridization of Crop Plants, American Society of Agronomy—Crop Science of America, Madison, Wisconsin, pp. 549-563.

Yermanos, D.M. 1984. "Sesame growing: an idealized overview," Text of speech given in Cairo, Egypt, 4 pages.

Zanten, L.Van (ed.) 1996. "Conclusions and Recommendations," 2nd FAO/IAEA Research Coordination Meeting, Antalya, Turkey, pp. 107-113.

* cited by examiner

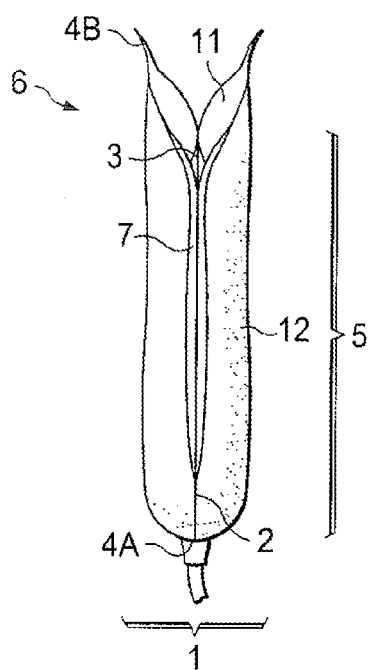 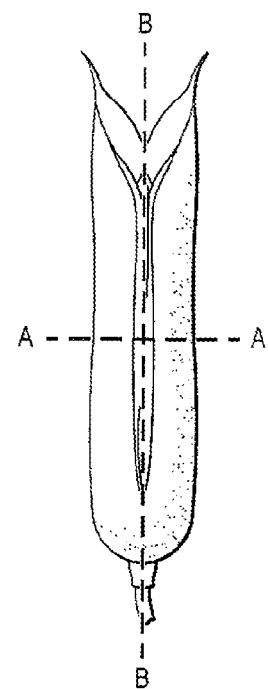
FIG. 1    FIG. 1A
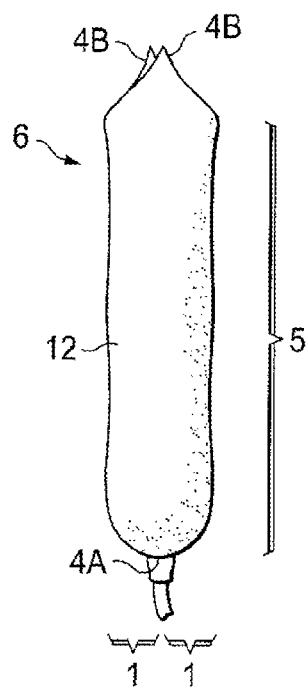
FIG. 2

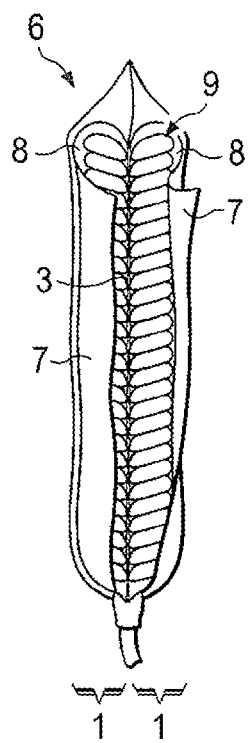
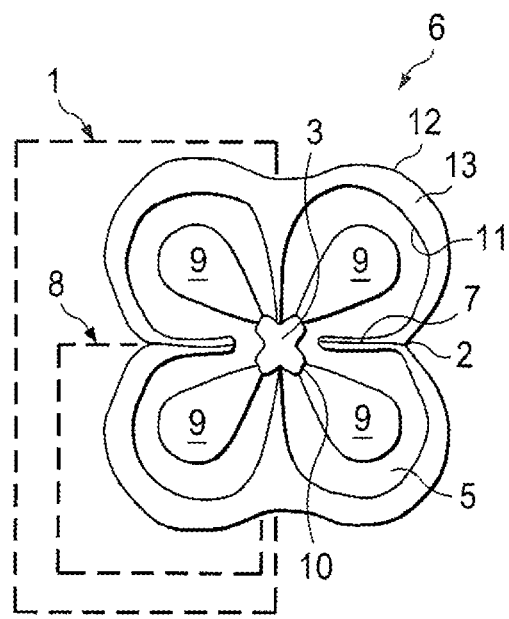
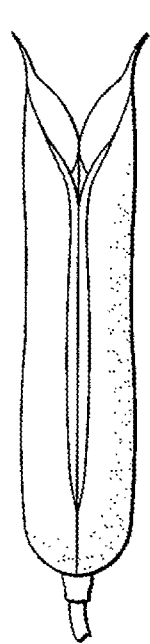
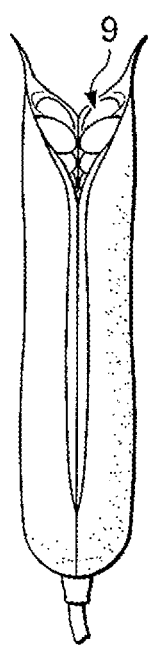
FIG. 3
FIG. 4
FIG. 5A
FIG. 5B

```
                        /G8   TP/TS + commercial characters
                /804
                 |     |    /111   TO/TM/TC
                 |     \111X
                 |          \BEE
         /K0338       /191   TP/TS/TM + commercial characters
          |      \96B
   /ZSA          \BEE
    |     |    /G8   TP/TS + commercial characters
    |    \S11      /111   TO/TM/TC
    |         \111X
    |              \BEE
/SAA
 |   |                /G8   TP/TS + commercial characters
 |   |         /B043
 |   |   /C063       \MEL   commercial characters
 |   \233       \G54   commercial characters
 |         \193   TP/TS/TM + commercial characters
13H
 |                /111   TO/TM/TC
 |         /111X
 |   /F820       \BEE
 |   /578         \104   commercial characters
 |    |     |    /104   commercial characters
 |    |    \F853
 \031         \192   TP/TS/TM + commercial characters
      \118   TS/TO/TM
```

FIG. 6

```
                          /G8   TP/TS + commercial characters
                 /S11        /111   TO/TM/TC
                  |       \111X
                  |           \BEE
           /88F      /192   TP/TS/TM + commercial characters
            |    \888
            |       \V52  commercial characters
            |                  /SOMALIA   commercial characters
  /BI791    |           /H6778
     |      |    /J3208     \118   TS/TO/TM
     |      |     |     |       /193 TP/TS/TM + commercial characters
     |      |     |    \H6432      /MAXIMO   commercial characters
     |      |     |       \076           /R234 commercial characters
     |      |     |            \R234 TALL
     |      /K3255                  \BEE
     |      |     |               /G8 TP/TS + commercial characters
     |      |     |        /045
     |      |     |   /H6785   \958   commercial characters
     |      |     |    |    |      /982   commercial characters
     |      |     |    |    \036
     |      |    \J3222       \G53.80-1   commercial characters
     |      |     |              /192 TP/TS/TM + commercial characters
     |      |     |        /195
     |      |    \H6562     \BEE
     |     \S16             \701  TS/TO/TM/TA
     |          /G8   TP/TS + commercial characters
     |       \S11      /111   TO/TM/TC
     |           \111X
     |               \BEE
88N       /G8  TP/TS + commercial characters
 |   /S11       /111   TO/TM/TC
 |    |    \111X
 |    |        \BEE
 \S17    /702  TS/TO/TM/TA
     \72A
         \BEE
```

FIG. 7

```
                        /702  TS/TO/TM/TA
            /7CB    /G8   TP/TS + commercial characters
                \804    /111  TO/TM/TC
                    \111X
                        \BEE
       /S22              /SOMALIA  commercial characters
        :           /FLXL
        :           :   \118  TS/TO/TM
        :           /FLXL   /193  TP/TS/TM + commercial characters
        :               \FLXL   /MAXIMO  commercial characters
        :                   \076    /R234  commercial characters
        :                       \R234 TALL
        :                           \BEE
        :       /FLXL           /G8   TP/TS + commercial characters
        :       :               /045
        :       :   /FLXL   \958  commercial characters
        :       :   :       /982  commercial characters
        :       :   \036
        :       \FLXL       \G53.80-1  commercial characters
        :                   /192  TP/TS/TM + commercial characters
        :               /195
        :           \FLXL   \BEE
        :               \701  TS/TO/TM/TA
        \FXA    /G8   TP/TS + commercial characters
            \S11    /111  TO/TM/TC
                \111X
                    \BEE
/HH450              /G8   TP/TS + commercial characters
        :           /804    /111  TO/TM/TC
        :               \111X
        :                   \BEE
        :   /K0338   /191  TP/TS/TM + commercial characters
        :       \96B
       /ZSA      \BEE
        :   :   /G8   TP/TS + commercial characters
        :   \S11    /111  TO/TM/TC
        :       \111X
        :           \BEE
       /SAA     /G8   TP/TS + commercial characters
        :   :   /B043
        :   /C063   \MEL  commercial characters
        :   \233   \G54  commercial characters
        :       \193  TP/TS/TM + commercial characters
        \13H            /111  TO/TM/TC
        :           /111X
        :       /F820   \BEE
        :   /578    \104  commercial characters
        :   :       /104  commercial characters
        :       \F853
        \031        \192  TP/TS/TM + commercial characters
            \118  TS/TO/TM
22J    /THB  commercial characters
  \22A    /702  TS/TO/TM/TA
     :    /7CB    /G8   TP/TS + commercial characters
     :        \804    /111  TO/TM/TC
     :            \111X
     \FDC          \BEE /SOMALIA  commercial characters
                    /FLXL
                    :   \118  TS/TO/TM
                /FLXL   /193  TP/TS/TM + commercial characters
                    \FLXL   /MAXIMO  commercial characters
                        \076    /R234  commercial characters
                            \R234 TALL
                                \BEE
            /FLXL           /G8   TP/TS + commercial characters
            :               /045
            :   /FLXL   \958  commercial characters
            :   :       /982  commercial characters
            :   \036
            \FLXL       \G53.80-1  commercial characters
                        /192  TP/TS/TM + commercial characters
                    /195
                \FLXL   \BEE
                    \701  TS/TO/TM/TA
        \FXA    /G8   TP/TS + commercial characters
            \S11    /111  TO/TM/TC
                \111X
                    \BEE
```

FIG. 8

```
                              /G8   TP/TS + commercial characters
                       /804
                        |     |    /111   TO/TM/TC
                        |    \111X
                        |          \BEE
                 /K0338    /191  TP/TS/TM + commercial characters
                 |         \96B
                 |             \BEE
           /ZSA              /G8   TP/TS + commercial characters
           |    \S11     /111   TO/TM/TC
           |        \111X
           |            \BEE
     /SAA                 /G8   TP/TS + commercial characters
     |    |          /B043
     |    |          |     \MEL   commercial characters
     |    |    /C063
     |    \233       \G54   commercial characters
     |         \193  TP/TS/TM + commercial characters
 /13H               /111   TO/TM/TC
  |    |             /111X
  |    |              |    \BEE
  |    |        /F820
  |    |         |    \104   commercial characters
  |    |   /578     \104   commercial characters
  |    |    |    \F853
  |    \031         \192  TP/TS/TM + commercial characters
  |         \118
S32              /G8   TP/TS + commercial characters
  |         /804     /111   TO/TM/TC
  |          |    \111X
  |          |        \BEE
  |    /56B     /111   TO/TM/TC
  |     |    /F822
  |     |     |   \192  TP/TS/TM + commercial characters
  |     |    \562
  |     |   \700   TS/TO/TM/TA
 \2CB         /702   TS/TO/TM/TA
   |   /L6651   /G8   TP/TS + commercial characters
   \2CA     \804    /111   TO/TM/TC
                \111X
                    \BEE
            /G8   TP/TS + commercial characters)
      \S11    /111   TO/TM/TC
          \111X
              \BEE
```

FIG. 9

METHOD FOR BREEDING IMPROVED NON-DEHISCENT SESAME

CROSS REFERENCE TO RELATED APPLICATIONS

This application is a divisional of application Ser. No. 12/041,257, filed 3 Mar. 2008, and now issued as U.S. Pat. No. 8,080,707.

STATEMENT REGARDING FEDERALLY SPONSORED RESEARCH OR DEVELOPMENT

Not applicable.

TECHNICAL FIELD

This invention concerns sesame plant breeding and providing sesame plant varieties appropriate for mechanized harvesting that are an improvement over current mechanized sesame varieties.

BACKGROUND OF THE INVENTION

Sesame, or *Sesamum indicum*, is a tropical annual cultivated worldwide for its oil and its nut flavored seeds. The sesame plant grows to a height of about 56-249 cm, and at its leaf axils are found capsules which contain the sesame seed. Upon maturity in nature, the capsules holding the sesame seeds begin to dry down, the capsules normally split open, and the seeds fall out. Commercially, the harvester tries to recover as much seed as possible from mature capsules. From ancient times through the present, the opening of the capsule has been the major factor in attempting to successfully collect the seed. Harvesting methods, weather, and plant characteristics all contribute to the amount of seed recovered.

The majority of the world's sesame is harvested manually. With manual non-mechanized methods, it is desirable for the sesame seed to fall readily from the plant. Upon physiological maturity, the sesame stalks are cut, tied into small bundles, and then stacked in shocks. Further harvesting procedures vary from country to country and from area to area within countries. Some move the shocks to a threshing floor so that the seed that falls out can be recovered. Others put plastic or cloth in the fields under the shocks to catch the seed. For manual harvesting methods in which the dried, shocked sesame is moved to a threshing floor or over a plastic or cloth, preferred plant varieties include dehiscent, or super shattering, in which less than 10% of the seeds set are retained in the capsule.

Other methods involve leaving the shocks in the fields, and when the shocks are dry, the sesame is turned upside down and struck with an implement to shake out all of the seed. For this type of manual harvesting method, it is preferred that plant varieties rated as "shattering" be used, wherein the capsule retains as much of the sesame seed as possible until the farmer inverts the stalk. Common methods of manual harvest are discussed in Weiss, E. A. "Sesame", *Oilseed crops* (2$^{nd}$ ed.), Chapter 5, Blackwell Science, Inc., Malden, Mass., p. 131-164 (2000).

In an effort to mechanize the harvest of sesame, D. G. Langham introduced the use of binders in Venezuela in 1944. The binders were used to cut and bundle the sesame plants, manual labor was used to shock the cut plants, and combines were brought in to thresh the shocks. This methodology is still used in Venezuela and Paraguay and is considered "semi-mechanized harvest" because it still requires some manual labor. It was determined that seed shattering during mechanized harvesting methods caused considerable loss of sesame seed. While mechanization was considered to be essential for crop production in the Western hemisphere, the dehiscence of the sesame seed capsule was the principal obstacle to the widespread acceptance of sesame as a commercial crop. (Langham, D. G. 1949. "Improvement of Sesame in Venezuela," *Proceedings First International Sesame Conference*, Clemson Agricultural College, Clemson, S.C., pp. 74-79). As programs to introduce sesame production in the United States in Arizona, South Carolina, Nebraska, Oklahoma, and Texas were initiated, mechanization was considered essential due to high labor costs. Kalton, one of the Texas researchers, reported that the shattering nature of available strains was the main obstacle in complete mechanization of the sesame crop. (Kalton, R. 1949. "Sesame, a promising new oilseed crop for Texas," *Proc First International Sesame Conference*, Clemson Agricultural College, Clemson, S.C., pp. 62-66).

In 1943, D. G. Langham found a mutation on a sesame plant. Capsules did not open on plants expressing this mutation. In succeeding generations, Langham showed that it was a recessive single gene which produced this indehiscence, where all the seeds were retained inside the unopened capsule. While it was believed that indehiscence would solve the problem of seed loss on mechanized harvesting, it was found that the capsules were too tough to effectively release the seed. Many of the capsules passed through a combine without opening. When more rigorous combining was attempted, an increase in efficiency of capsule opening was achieved but at the expense of seed quality. Seeds were broken due to the more rigorous combine conditions, and the broken seeds released free fatty acids. Chemical reactions with free fatty acids led to rancidity and concomitant undesirability of the harvested seed.

The indehiscent sesame varieties described above were used by various plant breeders in an attempt to develop desirable sesame lines. In addition to traditional cross-breeding approaches, some attempted to alter the chromosome numbers through tetraploids and interspecific crosses. Yermanos attempted to improve release of seed by increasing the length of the capsule so that there would be more surface for the combine to crack the capsules open (personal communication). Unfortunately, even with a small opening on the top of the capsule, a high percentage of broken seed was found on mechanized harvesting, preventing commercial use of this sesame line.

D. G. Langham reported in the late 1950's that the placenta attachment between each sesame seed and the placenta was important in the retention of seed in the capsule. He believed that he could improve the shatter resistance of sesame with increased placenta attachment but did not believe that all the seed could be retained in the capsule (Langham, D. G., Rodriguez, Maximo, and Reveron Esteban. 1956. "Dehiscencia y otras características del ajonjolí, *Sesamum indicum* L., en relación con el problema de la cosecha", Genesa, Maracay, Venezuela, pp. 3-16). However, Yermanos reported that during capsule maturity, the placenta attachment gradually weakens and is obliterated when the capsule is completely desiccated. (Yermanos, D. M. 1980. "Sesame. Hybridization of crop plants," *Am Soc Agronomy-Crop Sci of America*, pp. 549-563). Thus, it appeared that the placenta attachment would have little effect on seed retention in dry, mature capsules during harvesting. A seamless gene which retained all the seed in the capsules was discovered by D. G. Langham and D. R. Langham in 1986. (Langham, D. R., "Shatter resistance in sesame", In: L. Van Zanten (ed.), Sesame improvements by induced mutations, *Proc. Final FAO/IAEA Co-ord.*

Res. Mtng., IAEA, Vienna, TECDOC-1195, p. 51-61 (2001)). This was crossed with shattering types, and some progeny had an opening at the tip of the capsule. The seamless capsules were similar to the indehiscent capsules in that it was too difficult to remove the seed from the capsule without damaging the seed.

In 1982, the first non-shattering line (retaining 50-70% of the seeds set) requiring no manual labor was introduced. This line could be harvested by swathing the sesame, leaving it to dry in the field, and then picking it up by a combine. This methodology is fully mechanized, but it is rarely used because it uses two machines—one to swath and the other to combine. Although complete mechanization was achieved, extensive loss of seed due to adverse weather conditions continued to occur. (Langham, D. R. (2001), supra).

Other varieties were developed between 1988 and 1997 which allowed for direct combining which is the fully mechanized methodology that is currently used in the United States because it only requires one machine. With these varieties there was 70-90% seed retention, but extensive loss of seed due to environmental factors, such as wind and rain continued to occur. Lines that generally yielded 80% of the seed under ideal conditions would yield only 45-65% under adverse conditions. Thus, while many of the crosses began to moderate the deleterious effects of mechanized harvesting, none were able to increase the yields to the level of manually harvesting shattering cultivars.

A breakthrough was accomplished when non-dehiscent (ND) sesame was developed and patented by Derald Ray Langham. ND sesame was found to possess the proper characteristics which would enable mechanical harvesting without the seed loss disadvantages reported with prior varieties.

U.S. Pat. No. 6,100,452 which issued Aug. 8, 2000, disclosed a method for sesame breeding which resulted in ND sesame lines. Sesaco 22 (S22), Sesaco 23 (S23), Sesaco 24 (S24), 19A, and 11W, representative seed having been deposited under ATCC accession number PTA-1400, PTA-1401, PTA-1402, PTA-1399, and PTA-1398, respectively were examples of ND sesame lines which were made according to the claimed method. These sesame lines are characterized by their high degree of seed retention within the capsule despite adverse weather conditions such as wind and rain and the retention of a sufficient amount of sesame seed during mechanized harvesting to be competitive with manual harvesting with minimization of seed breakage.

U.S. Pat. No. 6,815,576 which issued Nov. 9, 2004, disclosed a non-dehiscent sesame cultivar S25, representative seed having been deposited under ATCC accession number PTA-4258. S25 is a stable, commercially suitable sesame line providing an early maturity cycle which extends the planting region to more northern latitudes and improved resistance against common fungal diseases.

U.S. Pat. No. 6,781,031 which issued Aug. 24, 2004, disclosed a non-dehiscent sesame cultivar S26, representative seed having been deposited under ATCC accession number PTA-4317. S26 is a stable, commercially suitable sesame line providing improved drought resistance, improved resistance against common fungal diseases, a larger seed, and a later maturity cycle which limits the planting region to more southern latitudes.

U.S. Pat. No. 7,148,403 which issued Dec. 12, 2006, disclosed a non-dehiscent sesame cultivar S28, representative seed having been deposited under ATCC accession number PTA-6008. S28 is a stable, commercially suitable sesame line providing improved resistance against common fungal diseases, a comparably large seed, and an early maturity cycle which extends the planting region to more northern latitudes.

U.S. Pat. No. 7,332,652 which issued Feb. 19, 2008, disclosed a non-dehiscent sesame cultivar S29, representative seed having been deposited under ATCC accession number PTA-6598. S29 is a stable, commercially suitable sesame line providing improved resistance against common fungal diseases, improved yields, and an early maturity cycle which extends the planting region to more northern latitudes.

New lines of sesame and methods for breeding the same are herein disclosed which are defined by a new category of dehiscence: improved non-dehiscence (IND) which provides improvements over previously disclosed non-dehiscent (ND) sesame lines.

SUMMARY OF THE INVENTION

In one aspect of the invention, a method for improving the mechanical harvesting of sesame crops via a machine adapted for harvesting, threshing and cleaning of grain crops is disclosed which comprises growing a sesame crop from improved non-dehiscent sesame seeds in a field, drying said sesame crop in the field to form a dried sesame crop which at a time $t_0$ is at the ideal harvest time, whereby said dried sesame crop can be harvested at a flexible time, said flexible time being at a time $t_1$ which is later than time $t_0$.

In another aspect of the invention, an improvement to sesame agriculture is disclosed, comprising utilizing agricultural land for planting of sesame crops wherein said land was previously deemed unsuitable for sesame as a crop due to adverse environmental factors. In the improvement, sesame crops comprising improved non-dehiscent sesame are planted which permits geographical diversification while retaining commercially acceptable yield.

In another aspect of the invention, a method for breeding sesame plants is disclosed to result in improved non-dehiscent sesame lines, comprising: crossing a plurality of sesame plants in a series of successive crosses, at least one of said plurality exhibiting a CAPSULE SPLIT rating of about 1 to 4, at least one of said plurality exhibiting a CAPSULE OPENING rating of about 5 to 8, at least one of said plurality exhibiting a CAPSULE MEMBRANE COMPLETENESS rating of 5 to 8, at least one of said plurality exhibiting a CAPSULE CONSTRICTION rating from about 3 to 6, at least one of said plurality exhibiting a CAPSULE MEMBRANE ATTACHMENT rating from about 4 to 8, and at least one of said plurality exhibiting a CAPSULE PLACENTA ATTACHMENT rating from about 4 to 8.

In other aspects of the invention, IND sesame plants and plant tissue are disclosed and claimed.

BRIEF DESCRIPTION OF THE DRAWINGS

FIG. 1 is an exterior view of a bicarpellate sesame capsule.

FIG. 1A is also an exterior view from the same vantage point of FIG. 1, but includes lines A-A and B-B for directional explanations in the text.

FIG. 2 is an exterior view of the capsule in FIG. 1 rotated 90 degrees about axis B-B.

FIG. 3 is a section of the capsule (6) taken along line B-B of FIG. 1A and rotated 90 degrees.

FIG. 4 is a cross section of the capsule (6) taken along line A-A of FIG. 1A as it appears twenty-five days after fertilization.

FIG. 5A depicts a non-dehiscent (ND) capsule 4 weeks after the field is ready for combining.

FIG. 5B depicts an improved non-dehiscent (IND) capsule 4 weeks after the field is ready for combining.

FIGS. 6-9 are crossing schematics for four improved non-dehiscent sesame lines.

FIG. 6 is a crossing schematic for Sesaco 13H
FIG. 7 is a crossing schematic for Sesaco 88N
FIG. 8 is a crossing schematic for Sesaco 22J
FIG. 9 is a crossing schematic for Sesaco S32

DETAILED DESCRIPTION OF THE INVENTION

Sesame plants have been studied for their response to seasonal and climatic changes and the environment in which they live during the different phases and stages of growth and development. This type of study, called "phenology", has been documented by the inventor in Langham, D. R. 2007. "Phenology of sesame," In: J. Janick and A. Whipkey (ed.), *Issues in New Crops and New Uses*, ASHS Press, Alexandria, Va.

Table I summarizes the phases and stages of sesame, and will be useful in describing the present invention.

TABLE I

Phases and stages of sesame.

| Stage/Phase | Abbrev | End point of stage | DAP$^z$ | No. weeks |
|---|---|---|---|---|
| Vegetative | VG | | | |
| Germination | GR | Emergence | 0-5 | 1– |
| Seedling | SD | 3$^{rd}$ pair true leaf length = 2$^{nd}$ | 6-25 | 3– |
| Juvenile | JV | First buds | 26-37 | 1+ |
| Pre-reproductive | PP | 50% open flowers | 38-44 | 1– |
| Reproductive | RP | | | |
| Early bloom | EB | 5 node pairs of capsules | 45-52 | 1 |
| Mid bloom | MB | Branches/minor plants stop flowering | 53-81 | 4 |
| Late bloom | LB | 90% of plants with no open flowers | 82-90 | 1+ |
| Ripening | RI | Physiological maturity (PM) | 91-106 | 2+ |
| Drying | DR | | | |
| Full maturity | FM | All seed mature | 107-112 | 1– |
| Initial drydown | ID | 1$^{st}$ dry capsules | 113-126 | 2 |
| Late drydown | LD | Full drydown | 127-146 | 3 |

$^z$DAP = days after planting. These numbers are based on S26 in 2004 Uvalde, Texas, under irrigation.

There are several concepts and terms that are used in this document that should be defined. In the initial drydown stage in Table I, the capsules begin to dry and open. This stage ends when 10% of the plants have one or more dry capsules. The late drydown stage ends when the plants are dry enough so that upon harvest, the seed has a moisture of 6% or less. At this point some of the capsules have been dry for 5 weeks in the example used in Table I, but in other environments for other varieties, the drying can stretch to 7 weeks. The "ideal harvest time" is at the end of the late drying stage. At this point, a combine (also sometimes referred to as a combine harvester, a machine that combines the tasks of harvesting, threshing, and cleaning grain crops) can be used to cut and thresh the plants and separate the seed from the undesired plant material. However, at times, weather may prevent harvest at the ideal time. The plants may have to remain in the field for as much as an additional four weeks, and in some cases even longer. Thus, time $t_0$ corresponds to the ideal harvest time and time $t_1$, which corresponds to the time the grower actually harvests the sesame is a time later than time $t_0$.

New lines of sesame have now been developed which define a new category of dehiscence: Improved Non-Dehiscence (IND). IND sesame exhibits improved characteristics of seed retention characteristics as compared with non-dehiscent (ND) lines previously disclosed and patented.

Prior to discussing the method of breeding disclosed and claimed herein, the characteristics of the IND sesame capsules will be detailed.

Sesame plants form capsules in the leaf axils of the plants, which capsules contain the sesame seeds. A sesame capsule comprises a seed chamber (defined by an epidermis layer, a mesocarp layer and an endocarp layer), and extends longitudinally from a base area to two tips. Referring now to FIG. 1 which shows capsule (6), base area (4A) and tips (4B) which are visible in this exterior view, bracket (5) references the portion of the capsule running along line B-B as illustrated in FIG. 1A where the seed chamber is located internal to the layers visible in this exterior view. Bracket (5) indicates a top and a bottom by the slightly extended lines at each end of the bracket. The outermost layer of the capsule is the epidermis (12) which is best illustrated by viewing FIGS. 1, 2 and 4. FIG. 4 is a cross section of FIG. 1, taken along line A-A as illustrated in FIG. 1A, and it can be seen that epidermis (12) is the outermost layer (the layer primarily visible before the capsule opens).

Now referring again to FIG. 1, the capsule further comprises a suture (2) visible from the exterior view of the capsule. In FIG. 1, the capsule has begun to split along suture (2) in the area longitudinally from the top indicated by the top of Bracket (5) towards the base (4A). The splitting has rendered false membrane (7) visible from the exterior view of the capsule. It was shown by Day that the false membranes separate two locules of one carpel (1). There are two carpels in a bicarpellate capsule. (See J. Day 2001. "The mechanism of indehiscence in sesame-features that might be useful in a breeding programme," p. 21-30. In: L. Van Zanten (ed.) *Sesame improvements by induced mutations*, Proc. Final FAO/IAEA Co-ord. Res. Mtng, IAEA, Vienna, TECDOC-1195).

Thus from the exterior view of the capsule as in FIG. 1, the structures of one of the two carpels of capsule (6) that can be seen are outermost layer or epidermis (12), suture (2) and false membranes (7). Suture (2) and false membranes (7) in this view are located along line B-B illustrated in FIG. 1A of one of the carpels. Also visible in exterior view FIG. 1 is the longitudinally uppermost portion of placenta (3). Placenta (3) extends from base area 4A upwardly along direction B-B in FIG. 1A, and is best seen in FIG. 3 which shows a section of the capsule along line B-B of FIG. 1A and in FIG. 4 which shows a cross section of the capsule along line A-A of FIG. 1A.

In exterior view FIG. 1, tips (4B) are also visible and one tip is in opposing configuration to the other tip. The inner layer of tips (4B) visible in FIG. 1 is a portion of the endocarp (11) of the second carpel of the bicarpellate capsule illustrated in FIG. 1 which second carpel starts at the apex of tips (4B). The exterior of the second carpel is not visible in FIG. 1 but if the capsule view in FIG. 1 is rotated 180 degrees around axis B-B shown in FIG. 1A, one would be able to see the exterior of the second carpel which would appear virtually identical to the view of the first carpel shown in FIG. 1. Single bracket (1) shown in FIG. 1 indicates the breadth of the single carpel of capsule (6) in this view.

Exterior view FIG. 2 represents a view of the capsule (6) illustrated in FIG. 1 which has been rotated 90 degrees about axis B-B as illustrated in FIG. 1A. In this view, epidermis (12) is visible as is the exterior of one half of said first carpel and one half of said second carpel, indicated by the Double Brackets (1) which each indicate the position of a half of distinct carpels. Each of tips (4B) is visible The cross section in FIG. 4 depicts two carpels of the capsule (6) as they would appear twenty-five days after fertilization and is taken along line A-A illustrated in FIG. 1A. In FIG. 4, from the outermost layer in, are illustrated the epidermis (12), mesocarp (13), endocarp (11) and false membrane (7), seed chamber (5) and seed (9) which is attached to placenta (3) at placenta attachment area (10). FIG. 4 is simplified for illustrative purposes. It should be noted that the mesocarp (13) comprises multiple layers of mesocarp (rounded parenchyma cells) and the endocarp layer comprises heavily lignified sclerenchyma cells. (See Day, supra,)

Each carpel normally has two locules. This is best illustrated in FIG. 4, which illustrates two carpels and four locules. One carpel of the two carpels illustrated is denoted by dotted line (1). Day, supra, demonstrated that each carpel has two locules that are separated by the false membrane (7). In FIG. 4, one of the four locules illustrated is denoted by the dotted line (8).

Still referring to FIG. 4, the position of suture (2) on the epidermis layer (12) is indicated for reference purposes. Note that the endocarp layer (11) is essentially continuous with the false membranes (7). The false membrane begins at a point contiguous with endocarp layer (11) and extends inwardly toward the placenta (3). Note that the character described herein of CAPSULE MEMBRANE ATTACHMENT can vary, and not all false membranes reach to the placenta.

FIG. 3 depicts a capsule which has been split completely along the suture (2) along direction B-B of FIG. 1A, thus revealing underlying false membranes (7) which separate the locules. Thus, in FIG. 3, one half of each of the two carpels is visible. In the center of the capsule, there is a placenta (3) that nourishes the seeds (9) during growth through a placenta attachment (10) (best seen in FIG. 4 at (10)). Again referring to FIG. 3, specifically to the left side of the drawing, the false membrane (7) obscures most of the seeds (9) secured to placenta (3), essentially from the base area (4A) to a position below tips (4B); however, whole seeds are visible at the top of the seed chamber. On the right side the false membrane has been pulled back for the purpose of illustrating how the seeds (9) lay within the seed chamber (5).

Most sesame in the Western Hemisphere is bicarpellate, but tricarpellate and quadricarpellate cultivars are found in Asia and Africa. It is expected that that IND lines can be made in tricarpellate and quadricarpellate cultivars using the method of this invention.

Normally, there is one row of 15-22 seeds per locule with about 60 to about 90 seeds per bicarpellate capsule. The average number of seeds per capsule is about 70.9 seeds per bicarpellate capsule. This is best seen in FIG. 3.

Within the carpels, the mesocarp layers are arrayed at a suture to allow a splitting within the carpels. The force of the splitting is provided by the drying of the mesocarp cell layers.

The shaker shatter resistance test developed for the ND lines previously disclosed and patented is explained in U.S. Pat. No. 6,100,452, which is herein incorporated by reference as if set forth in its entirety herein. This test involves 10 capsules taken from 5 plants and is known as the "10cap test." The shaker shatter resistance test indicates the projected amount of seed retention three months after the ideal harvest time.

This shaker shatter resistance test has been verified on 11,285 samples. Lines designated as ND by the shaker test have proved to retain their seed in several nurseries left in the weather 2-4 months after the ideal harvest time. For example, a line with a 75% seed retention in the laboratory will have at least 75% seed retention in the field as long as the plants do not lodge (fall over) from the wind. However, it has been found that there may be differences between two 75% seed retention lines in how fast they lose the 25% of the seed. The rate of loss is one of the basic differences between ND and IND lines—the IND lines lose the seed at a slower rate.

IND lines have less than 1 or 2 seeds missing in over 85% of the capsules four weeks after the ideal harvest time. The average number of seeds per capsule for all lines is 70.9. FIG. 5A-FIG. 5B depict a comparison between ND (FIG. 5A) and IND capsules (FIG. 5B) at four weeks post ready for combining. In essence, the seed can still be seen in the IND open capsule as shown in FIG. 5B, whereas in a ND capsule with 25% (17 seeds) of the seed gone, the seed cannot be seen in the capsule as shown in FIG. 5A—the capsule has to be opened to see how many seeds remain.

The previously patented ND lines S22, S23, S24, S25, S26, S28 and/or S29 have been observed to lose seed in the four weeks after the ideal harvest time. In comparison, IND lines have visible seed in over 85% of their capsules four weeks after the ideal harvest time. IND lines are further distinguished from indehiscent and seamless lines which hold their seed for the combine but do not release the seed without excessive damage to the seed.

Novel IND lines of sesame and methods for producing IND lines have now been developed. Concurrently filed and commonly owned U.S. patent application Ser. No. 12/041,205, is herein incorporated by reference, as if fully set forth herein. This application discloses Improved Non-Dehiscent Sesame Variety Sesaco 32 which is an example of IND. A sample of the seed of said variety has been deposited under ATCC Accession No. PTA-8888. In the method for producing IND lines, the breeder following sesame breeding methods known to the art may select appropriate sesame plants to cross with other sesame plants to result in progeny sesame plants having the desired characteristics of capsules to allow for better retention and less breakage of sesame seed during mechanized harvesting despite exposure of the sesame crop to adverse weather conditions such as rain and wind. These IND lines provide improved yields of commercially acceptable sesame seed from mechanical harvesting due to improved seed retention at 4 weeks after the ideal harvest time. IND sesame lines are a type of shatter resistant sesame identified by the amount of sesame seed retained in the mature, dry capsules. These lines must hold the sesame seeds in the mature, dry capsules on the plants in the field but must release the seeds within the combine as easily as possible without breakage of the seeds. As used herein, "broken" sesame seed is defined as large and small pieces of kernels of sesame seed which have been broken and which remain in the harvested sample after the removal of dockage (*Standards for Inspection and Grading of Sesame Seed*, Hudson Laboratories, Nov. 1, 1983).

The amount of seed retention is influenced by diverse characters of mature capsules which are manipulated through the present inventive method of breeding and selection processes to achieve IND. It has been found that sesame plants phenotypically expressing only one of these characters do not have enough shatter resistance to qualify as IND. However, in the method of the invention, multiple phenotypic characters become expressed in progeny plants through the disclosed breeding program methodology, and these multiple phenotypic characters provide the progeny plants with the desired IND. These characters with corresponding rating methodology are summarized in methodology for developing IND.

Capsule Characters Affecting Improved
Non-Dehiscence

The rating system used for providing values to the characters related to shatter resistance is a 0-8 scale. The ratings are done by examining 1 capsule from the middle of the capsule zone of the main stem of 10 plants and averaging the ratings. A subjective scale is used instead of measurements since the capsules vary considerably in length and width and has been found to effectively differentiate levels of shatter resistance. The expression of the character will also vary between capsules on the same plant and capsules on different plants. The ratings can be used to compare lines within a nursery in a given year, but do not necessarily apply across different locations and/or years. Hereafter, a baseline can be established each time the rating is employed by comparing all ratings to a well-characterized IND variety such as that disclosed by the inventor in concurrently filed patent application, S32. If a rated line is equal to or better than S32, it should be considered IND. The relative values obtained for different lines under given environmental conditions are valid indicators despite different locations and years. For example, two lines A and B can be tested side by side in Year 1, and values obtained for the characteristics described herein. The same two lines A and B can be tested side by side in Year 2, under different environmental conditions, and different numerical values may be obtained than were obtained in Year 1 testing. However, the values obtained in Year 1 comparing A to B and the values obtained in Year 2 comparing A to B will demonstrate the same like characteristics and the same differences.

The teachings of the prior ND patents detail six capsule characters that are important in developing ND. U.S. Pat. No. 6,100,452 which has been incorporated herein by reference provides details and figures which illustrate these capsule characteristics for sesame and can be referred to if desired. These same characters are important in developing IND with more emphasis on certain characters as shown by the two right columns of Table II. The ND column indicates the desired rating for an ND line, and the IND column the desired rating for an IND line. The key difference in the ratings is that the ND ratings are taken when the field is ready for combining whereas the IND ratings are taken 4 weeks post ready for combining, after being subjected to the environment.

TABLE II

Capsule Shatter Resistant Characteristics Used in Development of Improved Non-dehiscent Lines

| Character (Abbreviation) | Characteristics of the capsule | Rating/value System | ND | IND |
| --- | --- | --- | --- | --- |
| CAPSULE SPLIT (TS) | extent of split within the carpels exposing the membranes but not exposing seed | no split to complete split; scale of 0-8; 1 = split almost to base of the capsule, 4 = split halfway down capsule; 7 = barely split; 8 = no split; in capsules where there is a difference in split on each side of the capsule, the greater split measurement is taken | 1 | 1 |
| CAPSULE OPENING (TO) | extent of opening within the carpels with membranes opening enough to expose seed and/or seed chamber | no opening to complete opening; scale of 0-8; 1 = open almost to bottom of the capsule; 4 = open halfway down; 7 = barely open; 8 = no opening | 6-7 | 7 |
| CAPSULE MEMBRANE COMPLETENESS (TM) | amount of missing membranes on capsule within the carpels. The hole at the top of the membranes is normal and not considered in taking this rating. | complete membrane to no membrane; scale of 0-8; 0 = no membrane, 1 = most membranes incomplete, 4 = half of membranes incomplete, 7 = complete membranes, 8 = membranes with no holes | 7 | 7 |
| CAPSULE CONSTRICTION (TC) | degree of constriction of the capsule around the seeds as shown by the amount of seed remaining in the capsule after the placenta is removed | no constriction to good constriction; scale of 0-8; 1 = little seed, 4 = half the seed, 7 = most of the seed | 3-5 | 4-5 |
| CAPSULE MEMBRANE ATTACHMENT (TA) | amount of separation between the membrane and placenta | large to small separation between the membrane and placenta; scale 0-8; 0 = no membrane, 1 = large separation, 4 = medium separation, and 7 = little separation | 5-8 | 5-8 |
| CAPSULE PLACENTA ATTACHMENT (TP) | strength of placenta attachment | no to good placenta attachment scale of 0-8; 1 = minimal placenta attachment, 4 = some placenta attachment, 7 = good placenta attachment | 6-8 | 7-8 |

Capsule Opening (TO)

CAPSULE OPENING is one of the capsule characters for which the requirements for IND are higher than for ND. As will be discussed further in the relation of dehiscence and the environment, a TO6 or less does not sufficiently protect the seed from the elements. There are no IND lines that have a TO6 or less whereas there are ND lines that have a TO6 but rarely TO5. This is also a character where a higher rating of 8 is not desired since a closed capsule interferes with the release of the seed from the combine.

Capsule Membrane Completeness (TM) and Capsule Membrane Attachment (TA)

The combination of CAPSULE MEMBRANE COMPLETENESS and CAPSULE MEMBRANE ATTACHMENT determines the amount of surface between the false membranes that split each carpel. Testing conducted subsequent to the disclosures in the ND patent has shown that there is another aspect that is important. Between the false membranes, there is a layer of cells that dries down as the capsule dries down. These dry cells provide an adhesion between the false membranes that will counter the capsule opening.

The level of adhesion is similar to that observed in the ubiquitous office product, the sticky note. The level of adhesion is adequate to keep the false membranes adhered to one another, but adhesion between the false membranes can be easily disrupted. It is desirable to have sufficient adhesion while the capsule is in the field, but not so much adhesion that would prevent the capsules from splitting and releasing their seed in the combine. It is important that this adhesion persist for preferably about 4 weeks or more after the ideal harvest time $t_0$ keep the capsule from further opening.

Capsule Constriction (TC)

All IND lines have sufficient constriction so that the seed in the capsules does not rattle when tested via a drum test herein described. In the drum test, the main stem of the sesame plant is bent in one direction sufficiently so that upon release it will return to its original position. Then two fingers on the same hand are used alternatively to strike in rapid succession the dry plant in the middle of the main stem. This action shakes all of the capsules slightly, and any loose seeds in the capsules will rattle sufficiently against the inner capsule walls to be perceivable by the human ear. The amount of rattle provides an indication as to how the plant will retain seed when exposed to the elements over time—the less the rattle, the better the final seed retention. Alternately, a dry capsule can be taken from the plant and shaken next to the ear. A rattle is perceivable if loose seeds are in the capsule.

The drum test as described above has been employed by the inventor since 1992 as an indicator of seed attachment and correlation to final seed retention. In approximately 2001, the inventor noted dry sesame plants tested with the drum test that exhibited no perceivable sound even after being left in the weather for many weeks. The inventor used some of these plants to develop the method for breeding the IND lines and successfully developed IND lines.

Capsule Placenta Attachment (TP)

The level of CAPSULE PLACENTA ATTACHMENT is an important attribute of IND sesame. On the majority of prior known sesame lines, when the capsules first open, the TP rating is often TP7 to TP8, but quickly breaks down upon exposure to even slight breezes and/or abrasion such as the rubbing of capsules against neighboring plants or other capsules. With such a breakdown of the placenta, seeds begin to fall out of the capsules. This has been described in the literature: Yermanos, supra, described the PLACENTA ATTACHMENT as weakened and obliterated in dry capsules.

In IND sesame, placenta attachment does not weaken on drydown. The ideal CAPSULE PLACENTA ATTACHMENT is one that will hold the seed in the capsules even for an extended period after the ideal harvest time when exposed to the elements. However, the CAPSULE PLACENTA ATTACHMENT must be weak enough to release the seed once the capsule is inside the combine. The IND lines described herein are the first lines to exhibit the level of CAPSULE PLACENTA ATTACHMENT which provides for holding the seeds for an extended period in the field, even under adverse weather conditions but releasing the seed within the combine while harvesting with little or no damage to the seed.

IND lines may have variations in the amount of CAPSULE PLACENTA ATTACHMENT within the capsule. Good CAPSULE PLACENTA ATTACHMENT at the base of the capsule is not essential when there is good attachment at the top of the capsule. If the seed is held well at the top, it will block the bottom seed from exiting the capsule.

The increased amount of seed at the tip of the IND lines may be due to several factors. Without wishing to be bound to a particular theory, the inventor believes that the strength of CAPSULE PLACENTA ATTACHMENT (TP), the degree of CAPSULE OPENING (the closer the tips of the capsule opening, the better protection of the seed) and/or CAPSULE CONSTRICTION (TC) (a higher amount of constriction reduces rattling and puts less pressure on the seeds at the tip) may all contribute to increasing the amount of seed at the tip, in comparison to ND lines and other sesame lines.

Methodology for Developing Improved Non-Dehiscent (IND) Sesame

By incorporating the above-identified shatter resistant characters into commercially suitable sesame lines, IND sesame lines have been developed. The starting point for developing IND sesame is the same as used for developing the non-dehiscent sesame disclosed in U.S. Pat. No. 6,100,452 which is the acquisition of lines which have the shatter resistant characters. Representative sources for sesame lines necessary for the development of non-dehiscent sesame lines include the National Seed Storage Laboratory (NSSL) in Ft. Collins, Colo., and the Plant Genetic Resources Conservation Unit (S9) in Griffin, Ga. These collections were also deposited with the Food and Agriculture Organization of the United Nations (FAO) sesame collections maintained in South Korea and Kenya. In order to ensure the purity of these lines, one can grow out the materials for a year before selecting initial parent plants with required capsule characters. Table III provides representative sources for the different capsule characters required for developing non-dehiscent sesame and improved non-dehiscent sesame, and reference to specific lines and crosses in the following discussion are made by SID codes.

TABLE III

Sources for Capsule Characters Used in Development of Improved Non-dehiscent Sesame

| SID[a] | Sesame PI Number[b] | TS | TO | TM | TC | TA | TP | Neg CC[c] |
|---|---|---|---|---|---|---|---|---|
| 111 | PI 173955 |  | X | X | X |  |  | X |
| 118 | PI 426944 | X | X | X |  |  |  | X |
| 191 | [d] |  | X | X |  |  | X |  |
| 192 | [d] |  | X | X |  |  | X |  |
| 193 | [d] |  | X | X |  |  | X |  |
| 700 | PI 292144 | X | X | X |  | X |  | X |
| 701 | PI 292145 | X | X | X |  | X |  | X |

TABLE III-continued

Sources for Capsule Characters Used in Development of Improved Non-dehiscent Sesame

| SID[a] | Sesame PI Number[b] | TS | TO | TM | TC | TA | TP | Neg CC[c] |
|---|---|---|---|---|---|---|---|---|
| 702 | PI 292146 | X | X | X |   | X |   | X |
| ACE | PI 320959 | X |   |   |   |   | X |   |

[a]Significant lines were given three character sesame identifiers (SID).
[b]NSSL and S9 identifying codes.
[c]Negative commercial characters
[d]Commercially available sesame lines having sesame PI numbers 599447 through 599506 have a considerable amount of placenta attachment. One of these sixty lines (192) was a segregating population that was selected into SIDs 191 and 193. While these lines were obtained from the same researcher who supplied Ft. Collins, different identifiers were used. If the same order in numbering the lines was maintained by Ft. Collins, the PI number for 192 is PI 599464.

Using the methodology disclosed in the ND patent, over one thousand ND lines have been developed. Crossing lines in sesame is a straightforward procedure as disclosed in the ND patent.

In developing IND lines with positive commercial characters and eliminating negative commercial characters, the multiple genes that determine ND have to be moved concurrently. In crossing an ND line with a shattering line one will obtain no ND plants in the F1 generation. In the F2 there are 0-2% plants with some degree of shatter resistance, but true ND is not developed until the F3-F5 with the majority of selections being discarded based on shatter resistance alone, not including discards from presence of negative characters.

Although crossing between two ND lines usually results in an ND line, many times it does not. To obtain an IND sesame line, multiple crosses need to be made, and as with the ND development, once one IND line is obtained, more IND lines can be developed at a much faster rate. The examples in FIG. 6 and FIG. 7 are two lines that showed IND and yet did not become varieties. However, in using these two lines as parents, more IND lines were developed. Presently, over sixty IND lines have been developed with the method of the invention.

Field Methodology

In 1984 when the first plant was found with improved shatter resistance (804 in FIG. 6 and FIG. 7), the seed in the capsules looked like those illustrated in FIG. 5B. These types of capsules have been seen since 1956, but it was noted by the inventor that what distinguished this plant was that most of the capsules on the plant had seed to the top. In planting out this plant in 1985, some plants had low seed retention, some had medium seed retention, and few had the amount of seed retention seed desired. Through further selection, there was an improvement in the amount of seed retention, but it still averaged below 60%. The Sesaco 11 variety, released in 1988, and was the first variety that could be combined directly with an economical yield.

The drying phase as shown in Table I can take as long as 5 weeks. The capsules are the first to dry with the stem being the last to dry. Thus even though most of the capsules on a plant may look like FIG. 5B when they dry down, most will start losing seed before the stem dries down. The ND lines hold most of their seed through the drying phase to the ideal harvest time. The IND lines will hold most of the seed an additional four or more weeks after the ideal harvest time.

In order to develop IND lines, the inventor made use of the "drum test" previously discussed. While ND sesame plants exhibited a degree of audible rattle, those with higher amounts of rattle were found to not hold to seed at the completion of the drying phase. Such ND lines are not employed in the IND program.

Herein disclosed is a method of utilizing sesame lines for breeding IND that does not exhibit rattle in the drum test. In an exemplary method, two lines found by the inventor to exhibit no rattle (13H and 88N in FIGS. 6 and 7) were followed and were purified. It was further noted that the capsules had, the major character of CAPSULE CONSTRICTION. These lines were subsequently used as parents to get other IND lines to include 22J (FIG. 8) and Sesaco 32 (FIG. 9). These or other lines which do not exhibit rattle in the drum test may be used in a method for breeding IND.

In a preferred method, sesame lines are tested with the drum test as an initial indicator. However it is herein disclosed that improved success may be achieved by using a system of subjective screening measurements to also select plants that are negative for seed rattle but also will retain their seed four weeks after drying since some lines which initially have no rattle will not hold their seed 4 weeks after the ideal harvest time. It has been found that even where CAPSULE CONSTRICTION persists, PLACENTA ATTACHMENT may weaken the adhesion between the false membranes may weaken leading to a lower CAPSULE OPENING rating (less protection for the top seeds). As a result, the drum test is used only as an initial indicator but a system of subjective measurements is preferably used as well in selection of sesame for the breeding method of the invention.

The drum test is evaluated by an audible perception means which may be the unaided human ear, a human ear which is adjacent to a sound amplification device, or an electronic sound detection device such as a recorder. It is envisioned that a computer program could be written to evaluate and rate the sounds produced in the drum test. Most preferred due to its simplicity is use of the unaided human ear, which is able to perceive the rattling of seeds in the capsule. For large scale screening, an electronic sound detection means coupled with a computer program designed to evaluate said sound may be used and may be preferred due to the size of the screening.

Subjective Seed Retention Screening Measurement

The ND patent described an initial method for screening that involved using measures known as Upright Seed Retention and Inverted Seed Retention. This methodology was used until 2000 when there was a simple numerical Visual Seed Retention rating that paralleled the Upright Seed Retention rating described in the ND patent. In 2002, "X", "V−", "V", and "V+" were substituted for the numerical rating. In 2004, after more IND plants were seen, a "W−", "W", and "W+" classification was added to the VISUAL SEED RETENTION rating. In 2007, after whole lines were proving to be IND, the "I" rating was added and replaced the "W+" rating. The Visual Seed Retention rating is used only for individual plants or for bulk selections where all of the plants have the same level of seed retention. Plots are rated with the IMPROVED NON-DEHISCENT VISUAL rating as described in Table IV.

TABLE IV

Characters used to rate seed retention

| Character | Rating | Methodology |
| --- | --- | --- |
| VISUAL SEED RETENTION Amount of seed in most of the capsules in the middle half of the capsule zone when the plant(s) are dry enough for direct harvest with a combine | Subjective rating based on the following values: X = <50% seed retention (unsuitable for direct harvest) C = 50-74% seed retention (unsuitable for direct harvest, but may segregate V or above in future generations) V = >74% seed retention (sufficient seed retention for 10cap testing) W = >74% seed retention on weathering in field after rains and/or winds I = in using the "drum test" the seed in the capsules do not rattle and >85% of the capsules on the plant(s) harvested have visible seed in the tips of the capsules four or more weeks after the ideal harvest time. The "I" rating is used for all of the capsules on the plant. '+' and '−' modifiers can be used. | This rating is used for plants that are being selected for advanced testing whether individually or in a bulk with all the plants having the same level of seed retention. Most "X" plants can be identified from the first capsule that dries since the seed will begin falling out immediately. A "C" (close to V) plant will have some capsules with seed and some without. A "V" (visual shatter resistance) plant can be identified when the first 50% of the capsules have dried, but a "V+" rating should not be used until the complete plant is dry and most of the capsules are showing seed retention. Some "V" plants can be upgraded to "W" after the dry capsules have been subjected to weather (rain and/or wind). "V" and "W" become non-dehiscent only after 10cap testing with about an 80% passing rate. 10cap testing is done on "I" selections have had about a 99% passing rate. The "drum test" consists of placing the fingers from one hand about ½ inch from the center of the main stem and then striking the stem alternately with one finger and then the other finger in rapid succession. The human ear can perceive degree of rattling over a range. IND is defined as having no rattle. Degree of rattle in this test correlates with loss of increasing amounts of seed as capsules are exposed to weather conditions. Comments: the ratings above should be made under normal conditions (600 mm of annual rainfall and 30 kg/ha of nitrogen) through high moisture/fertility conditions. In drought or very low fertility conditions, it has been observed that there is less seed retention. In addition, high populations may lead to low moisture or fertility causing less seed retention. If unusual environmental conditions are present, the effects should be taken into consideration prior to rating. |
| IMPROVED NON-DEHISCENT VISUAL RATING Amount of seed in most of the capsules in the plants in a plot four or more weeks after the ideal harvest time. | Value based on the average on a minimum of three plots of a subjective rating based on the percentage of capsules with visible seed. 8 < 100% 7 < 85% 6 < 70% 5 > 55% Z < 55% '+' and '−' modifiers can be used. For averages, 0.33 is added for a '+' and 0.33 is subtracted for a '−', e.g., "7+" = 7.33. | This rating is used for a plot or field that is being evaluated. The data is taken four or more weeks after the ideal harvest time. Estimate the percentage of capsules that have visible seed at the top. In the beginning in order to develop an eye for the rating, the evaluator should observe all of the capsules and rate each of them; get a counts of those with visible seeds and a count of total capsules; and compute a percentage. Once the evaluator is skilled, there is no need to count the capsules. There is a very high correlation between this rating upon visual evaluation and the amount of rattling generated by the "drum test" defined above. |

TABLE IV-continued

Characters used to rate seed retention

| Character | Rating | Methodology |
|---|---|---|
| | | Although retention can vary from plant to plant and even within a plant, the overall rating is correlatable with IND. In crossing between lines, in early generations there is a segregation of IND plants and non-IND plants. In this case the plot is given a rating of the majority of plants while the plants selected can have a higher rating which is reflected in VISUAL SEED RETENTION. The ratings that are cited in this character are for plots, but a ratings of 7 or 8 are only given if over 90% of the plants have the higher rating. |

To date the IND lines developed have been perfected by the breeding methods of selection and reselection. Table V shows the most probable outcomes of crosses. Table V will assist those practicing the method in improving sesame lines with "X" plants that they have a desirable commercial character that is not presently in the current varieties. Many of these commercial characters are controlled by multiple genes; thus the probability of segregating good seed retention and good commercial characters on a single plant is low. Success in obtaining the desired qualities in a single line may be higher when one builds a series of building blocks, i.e., develop lines with "N" plus desirable commercial characters, and finally use those in the crossing program to get a line with "I" plus desirable commercial characters.

TABLE V

Crossing results based on types of parents

| Parents[z] | F1 | F2 | Comments |
|---|---|---|---|
| X and N | X | X, C, and N Most X | Usually in the F2 there are less than 2% N and often zero N. Selecting C will also rarely end up segregating N. It is better to do enough crosses and plant out as many F2 plants as feasible and only select N plants. |
| X and I | X | X, C, N, and I Most X | Same as above |
| C and N | C | X, C, and N Most C | X are rare and although it is better to just select N plants, there are many C plants with good commercial characters that have the potential to segregate N. |
| C and I | C | X, C, N, and I Most C | Same as above |
| N and N | X, C, and N | X, C, N, and I Most N | X and C are rare |
| N and I | X, C, N, and I | X, C, N, and I Most N | X and C are rare |
| I and I | X, C, N, and I | X, C, N, and I Most N | X and C are rare |

[z]There is no reason to make a cross where one of the parents is not an "N" or "I"

In selecting F2 plants with a certain rating, there is a somewhat low probability that there will be F3 segregating plants with a higher rating, but one can use such a technique if there are no other higher rated plants in the F2. However, by the F3, it is rare to have a rating increase in the F4. By the F3, plants with less than an "I" rating should not be selected. On the other hand it is common for a plant to segregate some plants with a lower rating, e.g., an "I" plant in one generation will segregate lower ratings in the next generation. Most times it is only by the F5 that the lines are pure "I". There are lines that will pass the "drum test" but not pass the 85% seed retention test. To date, there are no lines that pass the seed retention 85% test and do not pass the "drum test".

Objective Shatter Resistance Measurement

The subjective ratings above are based on the judgment of the rater. These are used during the development on IND lines, but prior to considering a line ready for variety testing, there is an objective method that can be used to confirm the judgment. The procedure is done 4 weeks after the ideal harvest time.

Step 1—In 5 areas of a field with full populations (no gaps in the rows or adjacent rows), choose 4 dominant plants (as defined in Langham, D. R. 2007. supra, "In moderate to high populations, there will be dominant plants and minor plants. The dominant plants generally emerged faster and since early growth is a geometric progression, they end up with larger cotyledons leading to larger leaves and deeper roots. These dominant plants will begin shading the other plants which will end up shorter with lower production. Compared to the dominant plants, the minor plants will start flowering later, will stop flowering sooner, and will dry down sooner.")

Step 2—Count the total number of capsules on each plant.

Step 3—Count the total number of capsules on each plant where the seed is not visible to the top of the capsule.

Step 4—Calculate the percentage of capsules where the seed is visible to the top of the capsule. If this percentage exceeds 85% then the line has Improved Non-dehiscence.

Seed retention is the first half of determining if a line is IND. The second portion of the IND and this patent is that the capsules need to release their seed in the combine with minimal damage to the seed. (There are lines that have too much seed retention and will not release the seed in the combine without severe threshing and damage to the seeds. The indehiscent and seamless lines fall in this category, but there are also lines with a capsule opening that have too much constriction, minimal capsule opening, and/or little capsule split that fall in this category).

Seed Release/Breakage During Mechanized Harvesting: Thresh Yield Tests

To test for the second requirement of IND sesame, i.e., high yield during mechanized harvesting, Examples 1 and 2 provide methods by which seed release and seed release/breakage, respectively, are determined. These are the same methods as defined in U.S. Pat. No. 6,100,452 for ND sesame.

Example 1

Plot Thresher Screening Method

Plot threshers can be used to screen for capsule seed retention vs. seed yield rates. Capsules taken from the plot thresher are opened and examined for seed retention. The capsules from IND lines have about 90% of the seed removed from the capsule by the thresher, while homozygous indehiscent lines, homozygous seamless lines, and lines with too small a capsule opening or too tight capsule constriction retain more than 10% of the seed in the capsules. While plot threshers provide an indication of the seed yield rate, they do not provide a measurement of seed breakage during mechanized harvesting. The plot threshers are, thus, used to identify crops which are subjected to the more definitive combine test.

Example 2

Combine Method for Measuring Seed Yield

The preferred method for the thresh yield test measures the amount of seed released and the amount of seed broken during harvesting in a combine. A sesame crop of not less than ten acres having a seed moisture content of about 6% or less is selected for combining. The combine is set for the field conditions such that the seed is threshed as gently as possible. Generally, this means a low cylinder speed and wide open concaves. For example, a John Deere 9600 combine is adjusted to the lowest cylinder speed with the concave adjusted to the "corn" setting and air at the minimum setting; and while threshing, the concave is adjusted toward the "soy" setting until mature seeds are removed from the capsules. For initial settings for other makes and models of combines, refer to Langham, D. R., J. Riney, G. Smith, and T. Wiemers. 2008. Sesame Grower Guide. Sesaco Corporation, San Antonio, Tex. Most sesame will have capsules at the top of the plant that do not contain mature seed, and this immature seed is not counted in these tests because they will generally blow out of the back of the back of the combine. Once the combine is set to obtain 99%-100% release of seed with broken seeds at less than or equal to 2%, the seed gathered during the setting process is dumped.

To get a representative sample, the combining test is begun and continues until the bin is full up to the input auger. With a four foot probe, samples are taken from four locations in the combine bin, and the samples are co-mingled. While the combine is operating, at a minimum of 100 feet from the end of the field, five capsules are taken from each of twenty plants at positions ranging from the bottom to the top of the plant but not including the immature seed capsules at the very top. In the same area, a container such as an oil changing pan is thrown between the wheels of the combine as it passes to catch the capsules that have gone through the combine and are going over the top of the screens/sieves. This procedure is repeated four more times.

In the laboratory, the seed is threshed out of the 100 capsules taken from the twenty plants, and the seed is weighed. At random, 100 representative capsules that came out of the combine and into the oil pan are selected. Seed from these capsules are threshed out and weighed. The weight of seed retained in the capsules is divided by the weight of the 100 capsules taken prior to combining.

The seed samples taken from the combine bin are thoroughly mixed and a 60 gram sample is taken. The seeds are separated into three groups: whole sesame seeds, broken seeds, and non-sesame chaff/foreign matter/immature seeds. After weighing the first two groups, the weight of the broken seeds is divided by the sum of the weights of the whole seeds and the broken seeds.

In IND lines, the capsules preferably retain less than or equal to about 10% of the seed during combining. Comparatively, indehiscent and seamless lines retain more than 10% of the seed during combining. More preferably, IND lines have less than about 7% broken seeds by weight after combining, whereas indehiscent and seamless lines have more than 7% broken seeds. Thus, IND lines are identified as having about 85% or more capsules with seed visible at the top from the capsule counting test, about 10% or less seed retention in the thresh yield test, and less than or equal to about 7% broken seed in the thresh yield test.

Advantages of IND: Machine Availability

IND provides advantages in commercial applications because an IND sesame crop enables greater flexibility in timing the harvest of the crop.

One of the problems that has affected sesame harvesting in the past is the ability of heavy equipment to access the fields where sesame is grown. Heavy rains may cause fields to be inaccessible to combine equipment when the sesame is ready for harvest. For example, in most areas of the world, sesame is grown in a season where the ripening and drying phases coincide with the end of a monsoon season. The majority of the sesame harvested in the world is done when there are no rains. In the United States, the ripening and drying phases coincide with the beginning of a period with higher rainfall, shorter daylight hours, and less heat. Depending on the soils and the amount of rain, a combine may not be able to enter a field to harvest the crop even if the plants and capsules are dry enough.

Another issue affecting sesame harvest is the need to harvest other crops at around the same in particular geographical areas. Competition for harvesting equipment and personnel may require that a choice be made between harvesting the sesame after the ideal harvest time and harvesting the other crop, which other crop may have time-dependent harvesting requirements of its own. For example, in some areas sesame, sorghum, soy beans, and cotton crops may be ready for harvest at the same time.

In other areas, sesame may be ready for harvest when other crops need to be planted. Again, this can present a conflict as to farming resources and personnel allocated to attending to the needs of each crop. For example, in some areas, sesame may be ready to harvest at the same time that farms must be planted with winter wheat.

IND provides an improvement in seed retention which permits greater flexibility in the time of harvest. The sesame crop may remain in the field longer and be subjected to weather conditions that would cause non-IND lines to lose seed. IND allows for less equipment to harvest the sesame because the seed will be retained longer. As just one example with ND sesame in the Rolling Plains of Texas in normal years, a farmer would maintain a ratio of 1 combine per 250 acres, whereas with IND sesame the ratio needed would be only be about 1 combine per 400-500 acres. Overall in all areas, the requirement for combines is decreased by 25% to 50% with employment of IND sesame.

Environmental factors—the so called "elements" discussed herein—have been known to influence the shatter resistance of the sesame capsule. Weather factors such as precipitation (rain, hail, fog, dew, etc) and wind can decrease the shatter resistance. Seed dispersal mechanisms also can decrease shatter resistance. On the other hand, sunshine, low wind and low humidity can increase shatter resistance. These factors will be discussed in more detail below.

Advantages of IND: Dispersal Mechanisms

In nature most plant species have evolved with systems that encourage seed dispersal for the perpetuation of the species. The sesame capsule opens when it dries down. With some lines there is a snapping noise and the seed flies out of the top of the capsule (mechanical dispersal). With other lines there is no sound and no mechanical dispersal. However, in such cases the capsule will continue to open more over time, and the seed contained therein will fall to the base of the plant.

Sesame lines can be tested for dispersal mechanisms by cutting green capsules from the plant and placing them upright in an appropriate container such as a beaker or jar. Under these laboratory conditions, most shattering lines will lose at least the top seeds, but others will be observed to lose all seeds. The latter observation has been made on sesame lines which do not have false membranes and which exhibit complete capsule splitting with the tips rolling back 180 degrees. These natural dispersal mechanisms have been reinforced by sesame farmer practices. In manual harvest, the plants are cut when they are green, tied in small bundles, and shocked to dry. The bundles are then inverted, and the seed falls out. Farmers discard mutations that do not allow complete seed release, and closed capsule mutations will not release their seed to advance to the next generation.

Advantages of IND: Weather

In direct harvest sesame the plants are left standing in the field until combined. Generally, within a plant there is no set sequence of drying although the capsules will dry down before the stems. In some lines the capsules at the bottom dry first and drying moves up the plant; in other lines the capsules in the middle will dry first and then the drying moves up and down the plant. Generally the stem will dry in the middle and move in both directions with the bottom part of the stem drying last. There is considerable variation in the drying phase as shown in Table I with the mean being 38 days and the range from 11 to 57 days. During drying, the capsules are exposed to weather.

The amount of rain direct-harvest sesame capsule is exposed to will affect seed retention. When a dry capsule gets wet, it will normally rehydrate. In ND and IND lines, the tips of the capsule will generally close up and then open again when the capsule dries. This opening and closing action weakens the adhesion between the false membranes and can lead to more capsule opening. If there is a heavy rain, most of the moisture falls to the ground and there is no rehydration and/or closing. A persistent drizzle will rehydrate the capsule. Heavy rains can lead to dews. Dew is the cause of the most common form of rehydration in that the moisture persists over a long period of time. There is more damage to the capsule integrity from dew than any other weather phenomenon. Depending on the dew, it usually does not affect all of the capsules (the lower capsules may be shielded by the upper plant). Fog can also affect capsule retention. There are many different types of fog and the duration of the fog is variable. However, fields planted near rivers and streams can be exposed to fog quite often. The amount of damage is commensurate with the amount of moisture as detailed above.

IND capsules withstand the moisture factors discussed above and hold the seed for combining. In practice, there can be 3 to 5 weeks from the time that the first capsules dry down until the ideal harvest time. Since IND capsules are able to withstand four additional weeks after the ideal harvest time, there can be as many as 9 weeks that individual capsules hold the seed as illustrated in FIG. 5B.

Heavy wind is another factor in shatter resistance. Wind can blow the plants back and forth in a whipping action and/or make one stem or branch rub against another. In whipping, there have been lines that bend with the wind where the plants blow to the point that the tips are horizontal and as the wind slows down, the tips whip back and thrust the seeds in the tips of the capsules out. There is more force in the capsules at the top of the plant and branches. In rubbing, the entire capsule can be rubbed off, but the action can also increase the amount of capsule opening. The stem quality and branching determine the amount of wind damage. Particularly in uniculm lines, there are stems that are strong enough that the wind does not twist or bend the stem so that there is little whipping or rubbing. In branching, the angle of the branch to the stem is important in that the tighter the branching the less the whipping and rubbing. The length of the branch also has an effect in that there is less whipping and rubbing on shorter branches.

The IND capsules can withstand the elements described above better than ND capsules because of the added strength of the placenta, the improved capsule constriction, and the improved capsule opening.

Advantages of IND: Geographical

There are certain geographical considerations to growing sesame crops. One consideration is temperature. The growing window of a crop as far as temperature is concerned is determined by the earliest the crop can be planted in the spring as the ground warms up, and the date of onset of cold weather in the fall. Current sesame varieties require about 21° C. ground temperature to establish an adequate population. In most years, the ground is warm enough in South Texas in middle April and in southern Kansas in late May. Current sesame varieties require night temperatures above 5° C. for normal termination. In most years, the night temperatures are warm enough in South Texas until middle November and in southern Kansas until middle October. East of Lubbock, Tex., the elevations begin climbing towards the Rocky Mountains, and there are later warm temperatures in the spring and earlier cold temperatures in the fall.

However, even where the temperature aspect of the climate is appropriate for sesame crops, adverse environmental factors such as excessive rainfall and/or other precipitation or moisture, the amount of wind in the geographical area and the likelihood of severe weather events have ruled out several areas of the United States and the world for growing sesame crops, despite the suitability of the climate as far as temperature is concerned.

For example, the otherwise suitable agricultural land may be located in climates which subject sesame to excessive wind at or after the time the sesame reaches ideal harvest time. This excessive wind would cause sesame other than improved non dehiscent (IND) sesame (the collective other sesame may be conveniently referenced as "non-IND sesame") capsules to lose seed in an amount which renders the yield of the sesame crop below commercial standards. Commercial standards for yield generally require a minimum of 65% of what the plant produces. By using the invention, even under adverse conditions, yield has been found to be higher than the commercially standard threshold-generally about 80-85%.

Along with wind, sesame capsules that are exposed to rainfall or moisture at a time when ideal conditions would permit sesame that has completed growing and is thereafter dried down to remain dry may also lose excessive seed. Particular geographic areas may statistically be at risk for such excessive moisture during this time frame. However, such geographical areas may be used in an improved method for growing sesame by planting IND sesame which can withstand the adverse environmental fact of excess moisture while retaining sufficient seed to meet commercial standards for yield.

An improvement to heretofore known methods for growing sesame crops which are capable of mechanical harvest with a combine harvester is now disclosed. The improvement comprises utilizing agricultural land for planting of sesame crops wherein said land was previously deemed unsuitable for sesame as a crop due to adverse environmental factors, said sesame crops comprising improved non-dehiscent (IND) sesame. The IND utilized preferably has a characteristic of DAYS TO PHYSIOLOGICAL MATURITY of 90-120 days, and preferably 105 days or less. This characteristic will be selected so that the environmental factors in the growing region can be correlated with the expected time of maturation and time $t_0$ as defined herein to minimize the influence of adverse environmental factors on the sesame crop.

The improvement to known methods for growing sesame crops is possible due to the ability of IND to hold its seed even in the face of adverse environmental factors which previously caused certain geographical areas to be ruled out for growing sesame crops. The prior importance or criticality of time $t_0$ corresponding to the ideal harvest time can now be ameliorated by the method of the invention which utilizes IND sesame seed. This allows harvest at a time $t_1$ which may be four to nine weeks after time $t_0$ while retaining or exceeding commercially acceptable yield.

I claim:

1. A method for breeding sesame plants to result in improved non-dehiscent sesame lines, comprising:
   crossing a plurality of sesame plants in a series of successive crosses, at least one of said plurality exhibiting a CAPSULE SPLIT rating of 1 to 3, at least one of said plurality exhibiting a CAPSULE OPENING rating of 5 to less than 8, at least one of said plurality exhibiting a CAPSULE MEMBRANE COMPLETENESS rating of 5 to 8, at least one of said plurality exhibiting a CAPSULE CONSTRICTION rating from 3 to 6, at least one of said plurality exhibiting a CAPSULE MEMBRANE ATTACHMENT rating from 4 to 8, and at least one of said plurality exhibiting a CAPSULE PLACENTA ATTACHMENT rating from 4 to 8; and
   screening progeny of any one of a series of successive crosses for non-dehiscent characteristics including greater than or equal to 85% of the capsules retaining essentially all of their seed in unharvested capsules four weeks after the ideal harvest time, seed is visible in 85% or more of the capsules four weeks after the ideal harvest time, less than or equal to 10% of the total amount of sesame seed is retained in mechanically harvested capsules, and less than or equal to 7% of the total amount of sesame seed released from capsules is broken during mechanical harvesting.

2. The method of claim 1, wherein said CAPSULE SPLIT rating is 1, said CAPSULE OPENING rating is 7, said CAPSULE MEMBRANE COMPLETENESS is 7, said CAPSULE CONSTRICTION is 4 to 5, said CAPSULE MEMBRANE ATTACHMENT rating is from 5 to 8, and said CAPSULE PLACENTA ATTACHMENT rating is from 7 to 8.

3. The method of claim 1, wherein at least one of said plurality exhibits non-dehiscence.

4. The method of claim 1, wherein said ratings for said CAPSULE SPLIT, said CAPSULE OPENING, said CAPSULE MEMBRANE COMPLETENESS, said CAPSULE CONSTRICTION, said CAPSULE MEMBRANE ATTACHMENT, and said CAPSULE PLACENTA ATTACHMENT are taken 4 weeks post ready for combining.

* * * * *